United States Patent [19]

Jones

[11] Patent Number: 5,683,399
[45] Date of Patent: Nov. 4, 1997

[54] ACETABULAR CUP INSERTION TOOL

[75] Inventor: Scott A. Jones, Eighty Four, Pa.

[73] Assignee: Stelkast Incorporated, Pittsburgh, Pa.

[21] Appl. No.: 566,093

[22] Filed: Dec. 1, 1995

[51] Int. Cl.⁶ .................................................. A61B 17/56
[52] U.S. Cl. .................................................. 606/91; 606/99
[58] Field of Search ................................ 606/91, 99, 100, 606/102; 279/2.01, 202, 2.09, 2.1, 2.11, 2.12, 2.15; 81/436, 442, 443, 444, 445, 453, 455; 600/214, 215

[56] References Cited

U.S. PATENT DOCUMENTS

| | | | |
|---|---|---|---|
| 319,095 | 2/1885 | Joel | 279/2.12 |
| 1,892,904 | 1/1933 | Robinson et al. | 279/2.12 |
| 2,393,587 | 1/1946 | Bugg et al. | |
| 3,479,722 | 11/1969 | Maness | |
| 3,709,546 | 1/1973 | Vaughan | 279/2.15 |
| 3,758,146 | 9/1973 | Kaercher, Jr. | |
| 4,305,394 | 12/1981 | Bertuch, Jr. | |
| 4,475,549 | 10/1984 | Oh | 606/91 |
| 4,632,111 | 12/1986 | Roche | |
| 5,030,221 | 7/1991 | Buechel et al. | 606/91 |
| 5,037,424 | 8/1991 | Aboczsky | |
| 5,059,196 | 10/1991 | Coates | |
| 5,061,270 | 10/1991 | Aboczsky | |
| 5,116,339 | 5/1992 | Glock | |
| 5,169,399 | 12/1992 | Ryland | |
| 5,171,243 | 12/1992 | Kashuba et al. | |
| 5,250,051 | 10/1993 | Maryan | 606/91 |
| 5,284,483 | 2/1994 | Johnson et al. | |
| 5,486,181 | 1/1996 | Cohen et al. | 606/99 |
| 5,540,697 | 7/1996 | Rehmann et al. | 606/91 |

FOREIGN PATENT DOCUMENTS 921806  10/1992  United Kingdom ................ 606/91

*Primary Examiner*—Michael Buiz
*Assistant Examiner*—Julian W. Woo
*Attorney, Agent, or Firm*—Kirkpatrick & Lockhart LLP

[57] ABSTRACT

The present invention provides an insertion tool and an associated acetabular cup implant. The tool includes a housing and an inner expansion pin for expanding the curved ends of resilient expandable arms of a collet on the distal end of the housing. The expandable arms engage corresponding curved surfaces in a groove in the concave surface of an acetabular cup. The tool also includes an actuation assembly which translates a slight rotation of a sleeve member on the housing to longitudinal movement of the expansion pin to radial expansion or contraction of the arms of the collet to engage or disengage the acetabular cup. A positioning assembly is also provided.

20 Claims, 6 Drawing Sheets

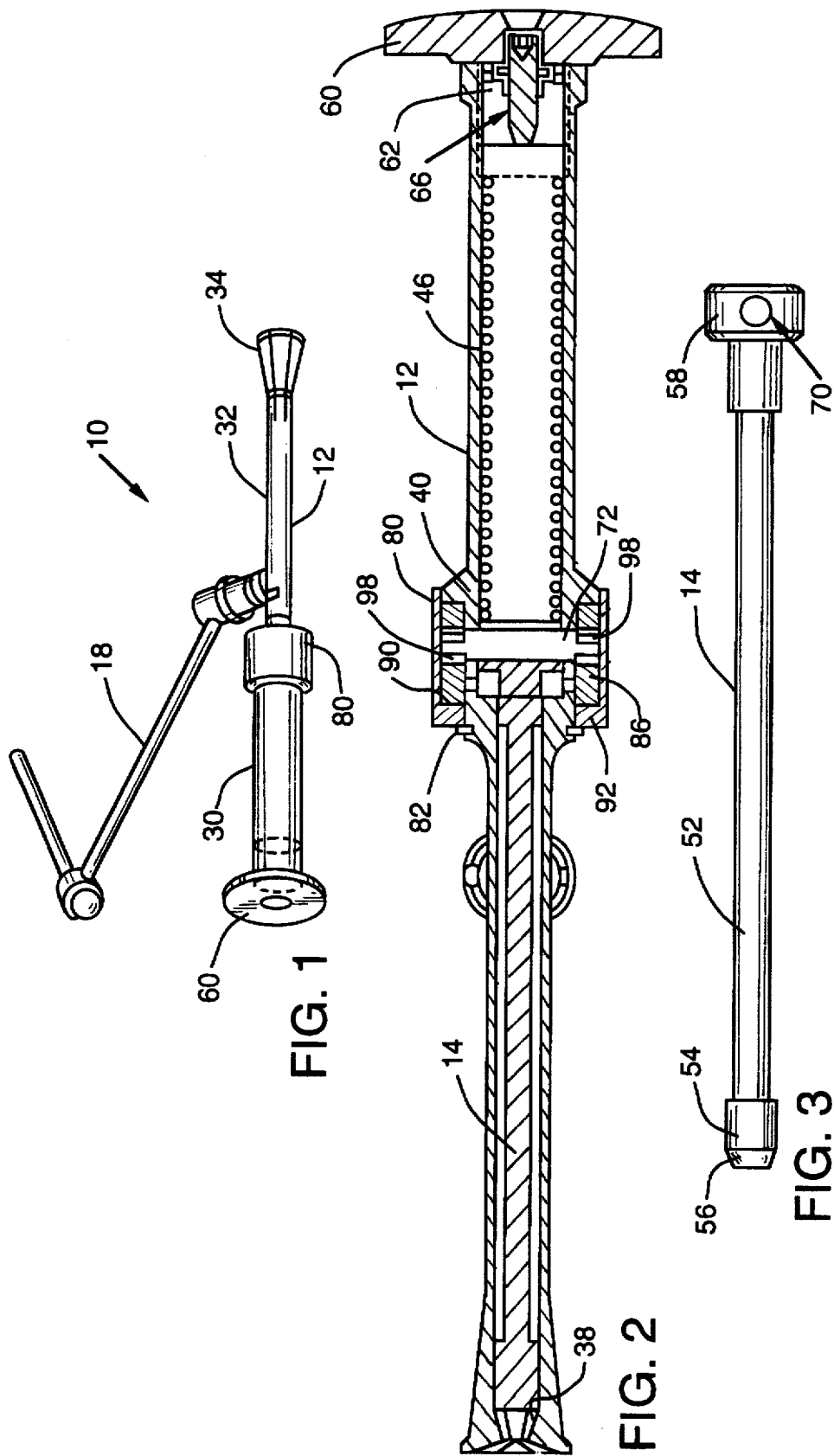

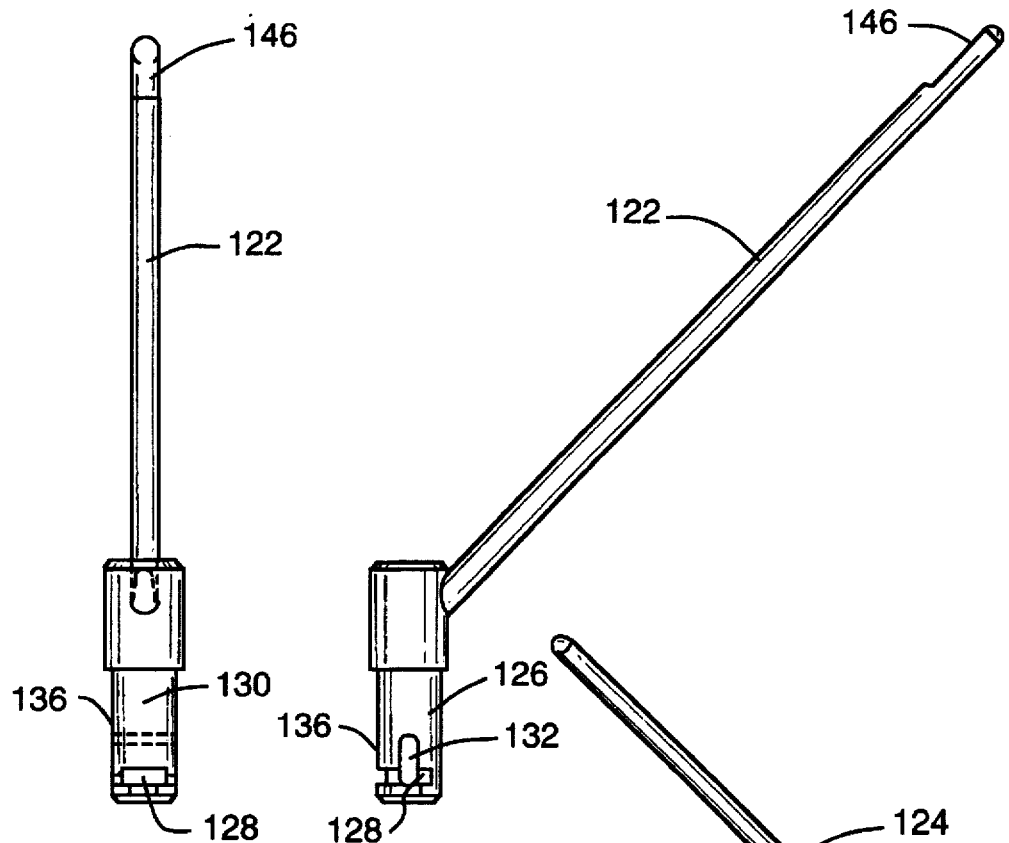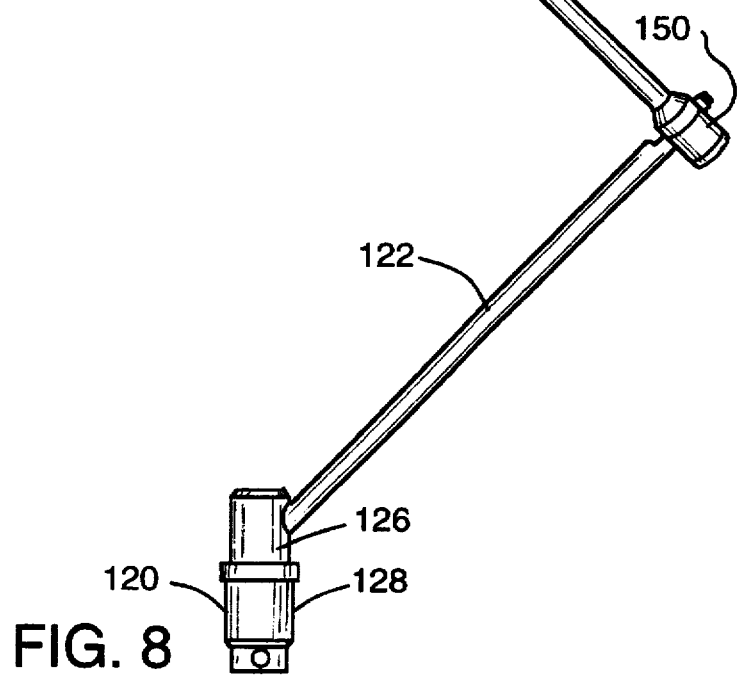

ACETABULAR CUP INSERTION TOOL

BACKGROUND OF THE INVENTION

1. Field of the Invention

The present invention relates to an instrument for insertion and removal of an acetabular cup implant in the proper anatomical position of a Patient.

2. Description of the Invention's Background

Acetabular cup implants are used to replace or repair the natural acetabulum in patients with severe hip injuries or degenerative bone disease. Proper positioning of the implant prior to affixation by the surgeon is critical to the patient's full and pain free use of the limb after recovery. Examples of insertion tools are described in U.S. Pat. Nos. 5,284,483; 5,171,243; 5,169,399; 5,116,339; 5,061,270; 5,037,424; 4,632,111; and 4,305,394. Many of the tools typically used to insert and properly orient the acetabular cup implants do not permit the surgeon to fully see the rim of the cup during insertion. Thus, before affixation, the surgeon may attach, disengage and reattach the insertion tool several times. Other tools rely on threaded engagement between the tool and the acetabular cup or various parts of the tool. In use, finding and turning the threads to engage and disengage the insertion tool is time consuming, thus adding to the time the patient is in the operating room. In addition, repeated threading causes the threads to gall.

SUMMARY OF THE INVENTION

There is a need for an insertion tool that does not require threaded engagement with the implant and that permits quick connection, release and reconnection of the tool to an implant for positioning the implant in the desired anatomical location. The present invention provides an apparatus that satisfies those needs. The apparatus of the present invention includes an elongate outer housing having a distal end and a proximal end and defining a hollow portion in at least the distal end thereof, an expansion member housed in the hollow portion of the outer housing, and an actuation assembly. The distal end of the expansion member includes a plurality of expandable gripping segments. The actuation assembly moves the expansion member between an extended position wherein the expansion member expands the gripping segments and a retracted position wherein the gripping segments contract.

The actuation assembly includes a rotatable shell on the outer housing operatively connected to the expansion member such that rotational movement of the shell causes the expansion member to move between the extended and the retracted positions. The actuation assembly also includes an actuation member for converting the rotational movement of the shell into movement of the expansion member.

The actuation member preferably includes a rotatable sleeve affixed to the shell for movement therewith. The sleeve has opposing semi-spiral pathways in the surface thereof and a pin operatively attached to a proximal end of the expansion member. The pin has opposing ends for sliding engagement with the pathways.

The expansion member may be in the form of an elongate rod having a distal end and a proximal end, the distal end having a beveled edge and the proximal portion having a member operatively connected to the actuation member and being configured for cooperation with the hollow portion of the outer housing for limiting the movement of the expansion member in the extended direction. A biasing member is preferably provided for biasing the expansion member in the extended position. The gripping segments preferably each have an inner ramped surface for sliding contact with the beveled edge of the distal end of the expansion member and a flared annular outer perimeter for locking engagement with the implant.

A cap is preferably provided on the proximal end of the outer housing to provide an impact surface.

The apparatus of the invention may also include an assembly for aligning the implant in the desired anatomical location for insertion. The aligning assembly preferably includes a member for mounting to the outer housing in a desired orientation, a first arm extending outwardly from the mounting member, and a second arm releasably connectable in a desired orientation to the first arm such that the second arm extends angularly from the first arm when connected thereto. The second arm is used for alignment with a remote anatomical location to thereby fix the orientation of the gripping segments relative to the desired anatomical location for insertion of the implant. The second arm preferably extends from the first arm at about a ninety degree angle and is connectable to the first arm in a left or a right orientation.

The outer housing of the apparatus preferably includes a mount and the mounting member of the aligning assembly preferably includes a post having a slot therein for receiving the mount on the outer housing in either a first or second desired orientation and a member for holding the housing mount in the slot.

While the insertion tool of the invention may be used with a variety of implants adapted for engagement with the tool, the tool is particularly useful for an acetabular cup implant having an outer surface, a generally concave inner surface, and an annular groove formed in the inner surface. The annular groove has curved surfaces complementary to the flared annular outer perimeter of the gripping segments for locking engagement with the gripping segments when the gripping segments are inserted in the groove and the expansion member is in the extended position.

BRIEF DESCRIPTION OF THE DRAWINGS

The invention and its advantages can be better understood by reference to the drawings which are illustrative of the preferred embodiment of the invention and are not intended to, and should not be construed to, limit the scope of the invention in any way.

FIG. 1 is a perspective view of the preferred embodiment of the insertion tool of the present invention.

FIG. 2 is a section view of the tool of FIG. 1.

FIG. 3 is a side view of the inner expansion pin of the insertion tool of FIG. 1.

FIG. 8 is a side view of the positioning assembly of the insertion tool of FIG. 1.

FIG. 9 is a side view of the inner portion of the mounting member of the positioning assembly of FIG. 8.

FIG. 10 is a front view of the inner portion shown in FIG. 9.

DETAILED DESCRIPTION OF THE PREFERRED EMBODIMENT

Figure 14:
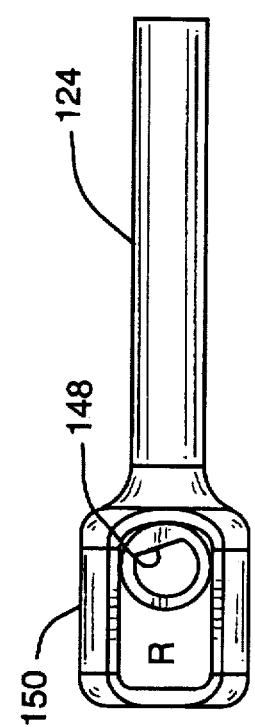
FIG. 14 is a partial view of the right orientation of the alignment member of FIG. 12.
Figure 15:
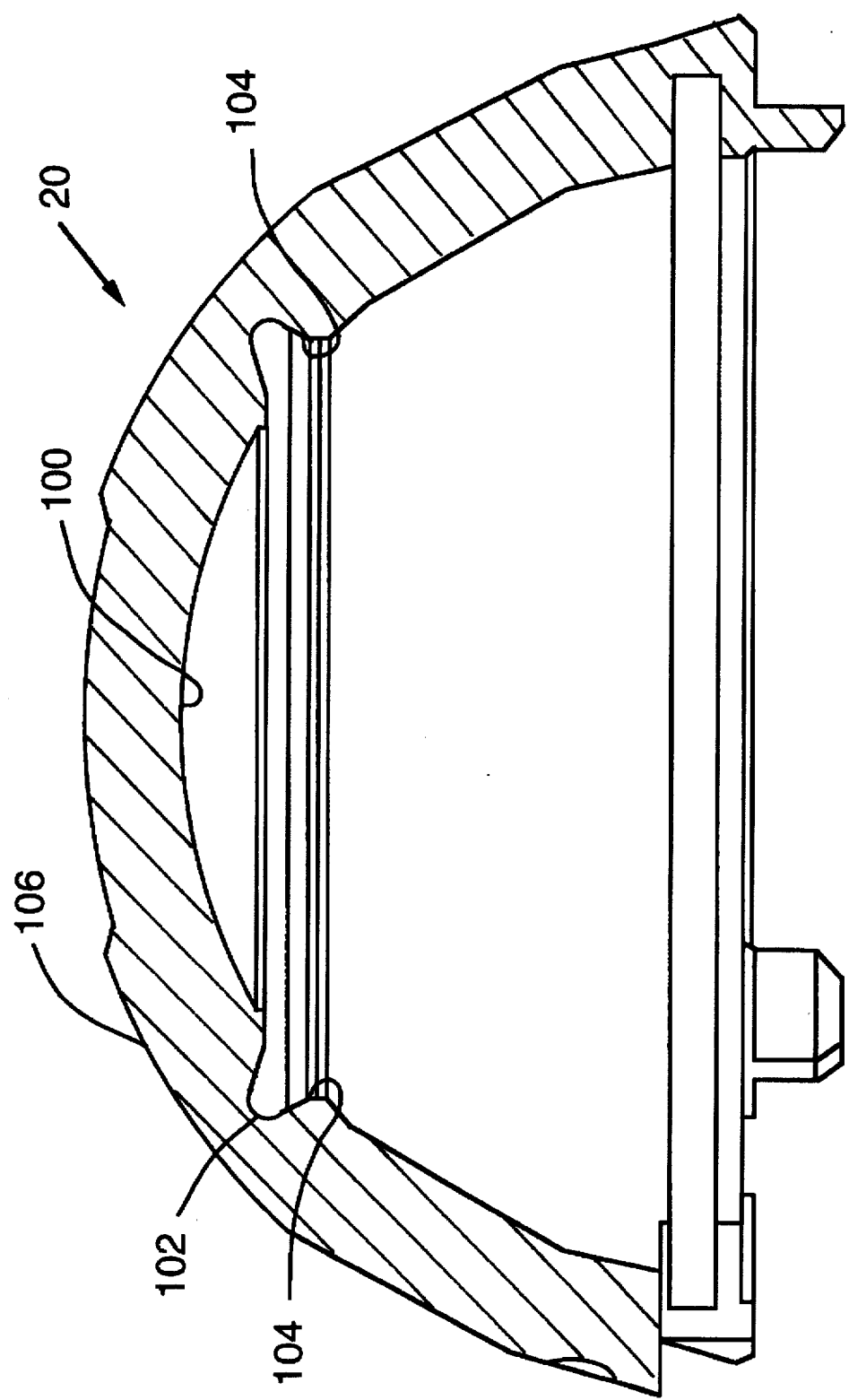
FIG. 15 is a section view of an acetabular cup designed for insertion and positioning with the insertion tool of FIG. 1.

The insertion tool 10 of the present invention is shown in FIGS. 1 to 14. An acetabular cup implant 20 for which the insertion tool 10 can be used for insertion and orientation is shown in FIG. 15. While the insertion tool will be described herein for use with an acetabular cup implant 20, those skilled in the art will recognize that the tool 10 can also be used with a trowel for preparation of the site and alignment before use with the actual implant 20. It will be further understood that the tool 10 of the present invention can be used with implants other than acetabular implants if the implants are adapted for use with the tool 10 as described more fully below.

Referring to FIGS. 1 and 2, the insertion tool 10 includes generally an elongate outer housing 12, an inner expansion pin 14, an actuation assembly 16 and a positioning assembly 18.

Figure 4:
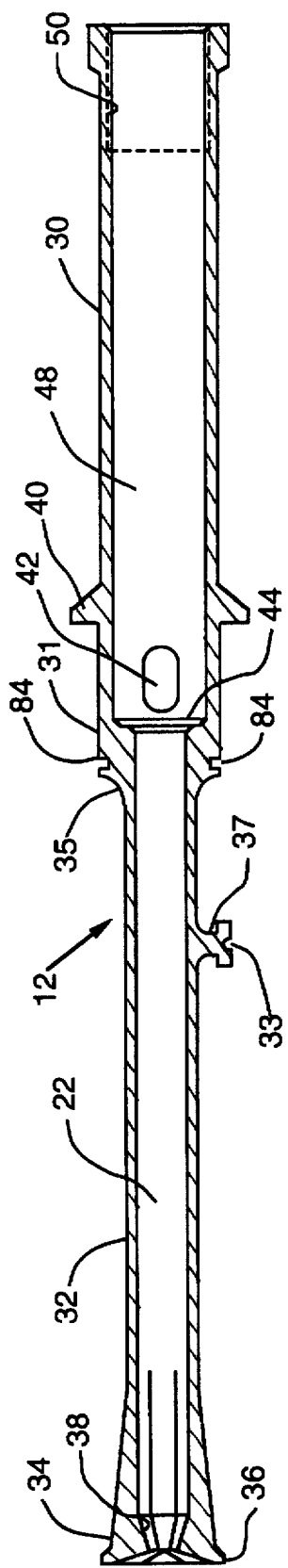
FIG. 4 is a section view of the outer housing of the insertion tool of FIG. 1.
Figure 7A:
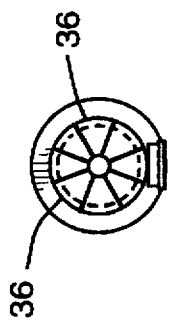
FIG. 7 (a) and (b) are end views of the expandable collet of the distal sleeve shown in FIG. 4.
Figure 7B:
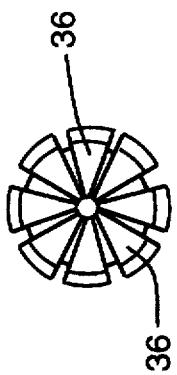

The housing 12, as shown in FIG. 4, is a hollow tubular member having a proximal portion 30, an intermediate section 31 and a distal sleeve 32. Distal sleeve 32 is smaller in diameter than proximal portion 30 and includes a bore 22. The end of distal sleeve 32 has an expandable collet 34 formed from resilient expandable segmented members 36. The outer edges of members 36 are flared along the perimeter thereof and rounded for a smooth locking engagement with complementary surfaces in the concave surface of the acetabular cup 20 (see FIG. 15) when the collet 34 is spread, as shown in FIG. 7(b) and described in more detail below. The inner edges of members 36 flare inwardly to form a ramped surface 38. A mount 37 is positioned on the external surface of distal sleeve 32 to mount the positioning assembly 18.

The intermediate section 31 of housing 12 extends from the external annular flange 40 to the curved transition 35 to the distal sleeve 32. Opposing oval shaped openings 42 are positioned between the flange 40 and the transition 35. The interior of housing 12 at proximal portion 30 and intermediate section 31 includes a bore 48 for receiving a biasing member, such as a spring 46, and a shoulder 44 intermediate bore 48 and bore 22. The proximal end of proximal portion 30 is open and includes internal threads 50. Cap 60, which is received in the open proximal end of portion 30, includes a truncated, externally threaded shaft 62 having a threaded bore for receiving a set pin 66. The shaft 62 may include slots to divide the shaft 62 into expansion segments. The set pin 66 causes shaft 62 segments to spread radially outward, thereby firmly locking cap 60 into place. A firm engagement is important so that cap 60 does not loosen during impact as the acetabular cup implant 20 is hammered into position.

The inner expansion pin 14, shown in FIGS. 2 and 3, extends through bore 22 to bore 48 in the interior of intermediate section 31. It includes an elongate shaft 52 and a distal head 54 at one end. The head 54 has a beveled edge 56 for sliding engagement with the ramped surface 38 of the segmented members 36 of collet 34. At the opposite end of shaft 52, expansion pin 14 includes a member 58 which extends into bore 48 for operatively joining expansion pin 14 to the actuation assembly 16. To this end, member 58 includes a through-hole 70 for receiving the shaft of actuation pin 72 of actuation assembly 16. Member 58 is dimensioned to slide freely in bore 48 within the limits imposed by spring 46 and actuation pin 72, but is restricted by shoulder 44 from entering bore 22, thereby limiting the extent to which head 54 of expansion pin 14 can move in the distal direction to its extended position.

Figure 6:
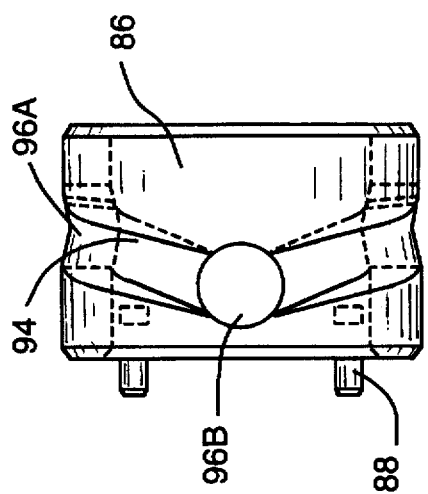
FIG. 6 is a side view of the portion of the cam assembly shown in FIG. 5.
Figure 5:
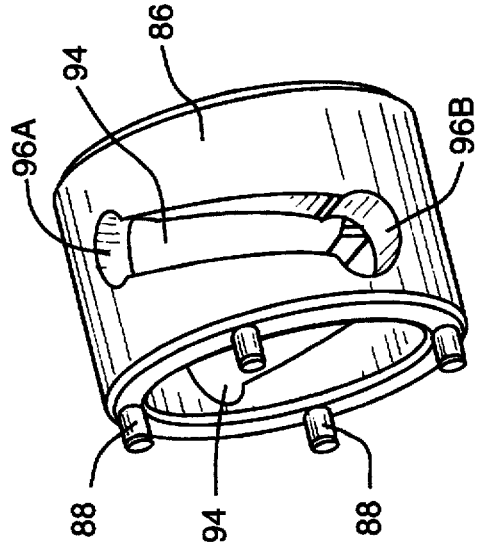
FIG. 5 is a perspective view of a portion of the cam assembly of the insertion tool of FIG. 1.

The actuation assembly 16, shown in FIGS. 2, 5 and 6, includes a rotatable annular outer shell 80 with a knurled outer surface for ease of handling. The shell 80 is held in position against longitudinal movement over the intermediate section 31 of housing 12 by a stop ring 82, a portion of which rests in groove 84 (see FIG. 4) on the surface of housing 12. The remainder of stop ring 82 extends beyond groove 84 to hold shell 80 in position. The shell 80 defines an annular space 90 between the interior of shell 80 and the exterior of intermediate section 31, bounded on one side by flange 40 and on the other by the collar 92 of shell 80. Assembly 16 also includes a rotatable actuation sleeve 86 which is positioned around intermediate section 31 in the annular space 90. Locking pins 88 lock actuation sleeve 86 to complementary female members in the collar 92 of shell 80 so that rotation of shell 80 causes simultaneous rotation of actuation sleeve 86 within annular space 90. Sleeve 86, like shell 80, is limited to rotational movement and is constrained against movement in the longitudinal direction, along the length of housing 12.

Sleeve 86 includes opposing semi-spiral pathways 94 with detents 96 A and B at the proximal and distal ends thereof, respectively, for receiving the ends of actuation pin 72 (see FIG. 2). Pin 72 has opposing ends of reduced diameter about which are positioned bearing members 98 to reduce friction as actuation pin 72 rides along pathways 94.

In use, expansion pin 14 is normally biased by spring 46 in the distal direction so that beveled edges 56 of head 54 ride along ramp 38 of collet 34 to radially expand the resilient segmented members 36 as shown in FIG. 7(b). In this extended position, bearings 98 rest in the distal detents 96 B. When shell 80 is rotated, sleeve 86 rotates forcing actuation pin 72 to slide within pathways 94 until bearings 98 come to rest in detents 96 A. By virtue of the joinder of actuation pin 72 to member 58 of expansion pin 14, the movement of the actuation pin 72 in the proximal direction along pathways 94 pulls expansion pin 14 back into a retracted position. Beveled surface 56 of head 54 slides in the proximal direction on ramp 38 to allow segmented members 36 to contract into the closed position shown in FIG. 7(a). Those skilled in the art will recognize that expansion pin 14 can also be biased in the retracted position instead of in the extended position as described by appropriate placement of a spring or other biasing means in bore 22 with suitable stops.

Referring to FIG. 15, the acetabular cup implant 20 of the present invention includes an outer, preferably convex surface 106 and an inner, generally concave surface 100. On the concave surface 100, there is an annular groove 102 having a curved surface for complementary engagement with the curved flared edges of segmented members 36 of the insertion tool 10. Groove 102 includes a curved shoulder 104 which creates a mechanical lock when the curved edges of segmented members 36 are in the expanded position. The insertion tool 10 can not be removed from the cup 20 unless the expansion pin 14 is retracted by rotation of shell 80 and actuation sleeve 86 so that segmented members 36 are allowed to assume the closed position. The mating curved surfaces allow maximization of the spherical surface of the implant 20 to thereby increase the contact area between the groove 102 and the collet 34 of insertion tool 10.

Figure 11:
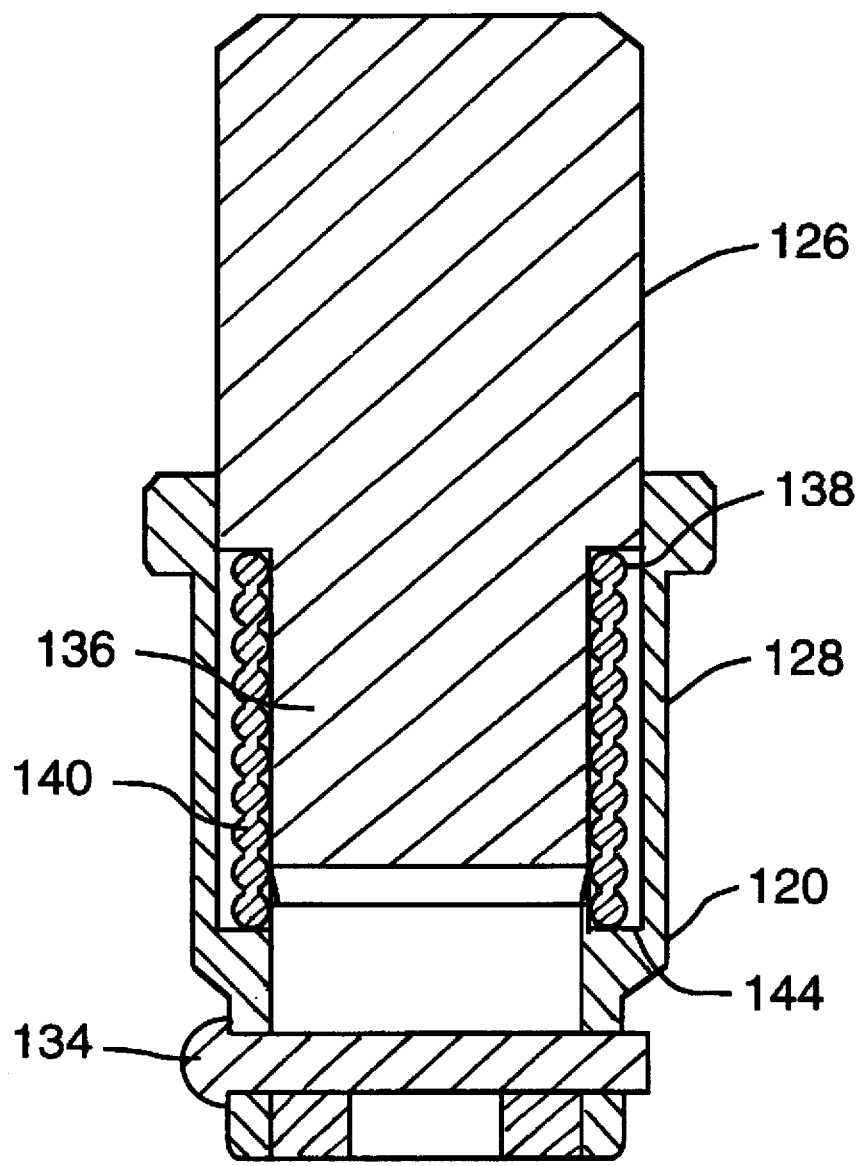
FIG. 11 is a section view of the mounting portion of the positioning assembly of FIG. 8.
Figure 12:
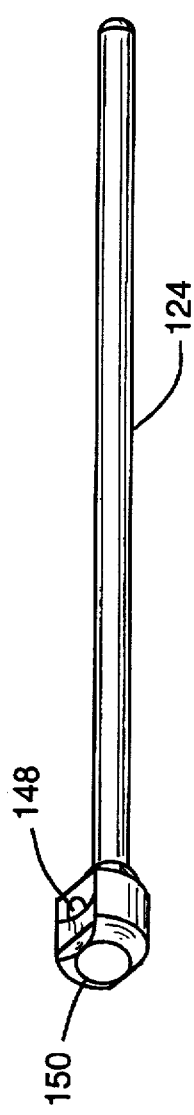
FIG. 12 is a perspective view of the alignment member of the positioning assembly of FIG. 8.

The positioning assembly 18, shown in FIGS. 8 to 14, includes a mounting member 120 and first and second alignment arms 122 and 124. Mounting member 120 includes a post 126 and an outer housing 128. Referring to FIGS. 9 and 10, there is shown a transverse slot 128 (transverse to the longitudinal axis 130 of post 126) and a longitudinal slot 132. Slot 128 is dimensioned to releasably receive mount 37 of housing 12. The depression 33 of mount 37 is positioned in use in alignment with longitudinal slot 132. Referring to FIG. 11, a pin 134 passes through a hole in outer housing 128, through the longitudinal slot 132 and rests on the depression 33 of mount 37. Outer housing 128 and pin 134 lock positioning assembly 18 to mount 37 which is fixed, preferably integrally attached, to housing 12. Post 126 includes a narrow portion 136 and a shoulder 138, which are received in outer housing 128. A space is defined between the narrow portion 136 and the housing 128 to hold a biasing member, such as spring 140, for biasing post 126 outwardly away from housing 12, and thereby locking onto mount 37. Spring 140 rests between shoulder 138 of post 126 and internal shoulder 144 of housing 128. When it is desirable to release the positioning assembly from mount 37, post 126 is lifted, and mount 37 is released from slot 128. Post 126 can be joined to mount 37 from two directions, allowing for variation in the orientation of the assembly 18 relative to the housing 12 and the direction of the desired anatomical location for the implant 20.

Figure 13:
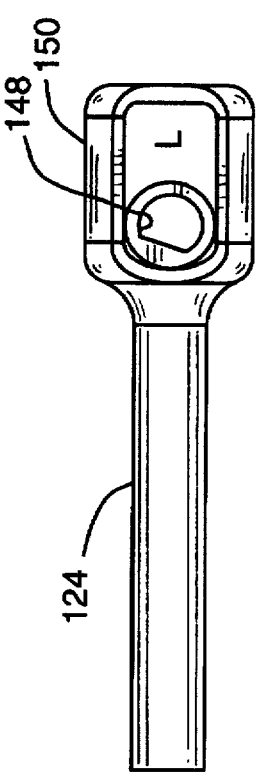
FIG. 13 is a partial view of the left orientation of the alignment member of FIG. 12.

First alignment arm 122 extends from the upper portion of post 126. The free end 146 of arm 122 has a flattened section for engagement in the complementary opening 148 of the junction end 150 of arm 124. In this way, arm 122 is aligned at a preferred ninety degree angle relative to arm 124. As shown in FIGS. 13 and 14, arm 124 can be positioned in a left or right hand orientation so that the insertion tool 10 and its positioning assembly can be used for implants on both the left and right sides of the patient. During a hip replacement procedure, the patient is lying on his or her side. In use, the second alignment arm 124 is pointed toward a remote anatomical location, such as the adjacent shoulder of the patient. Arm 124 can be removed from the end 146 of arm 122 for left or right positioning. The flattened complementary edges of end 146 and opening 148 prevent arm 124 from rotating relative to arm 122. By aligning arm 124 with the patient's shoulder, for example, the insertion tool 10 and the engaged acetabular cup 20 are pointed in the correct direction for alignment with the desired anatomical location for insertion of the implant 20. By changing the configuration of end 146 and opening 148, additional orientations can be obtained.

The insertion tool 10 and associated acetabular cup 20 of the present invention provide a quick means of engaging and disengaging the tool 10 and the cup 20. A quarter turn or less of shell 80, by rotating the shell 80 through the arc of an angle of about ninety degrees, will release or engage cup 20. That is a marked improvement over the time required to thread and unthread prior art insertion tools and cups. The quick engagement/disengagement made possible by the present invention reduces the time the patient needs to spend in the operating room and under anesthesia. The insertion tool 10 of the present invention is streamlined and the manner in which it engages the complementary grooved surface of the acetabular cup 20 allows the surgeon to have full view of the cup 20 while it is being positioned. There are no bulky mechanisms to block the view of the rim of the cup 20. Further, the insertion tool 10 is ergonomically designed for balance, ease of handling and avoidance of strain.

What is claimed is:

1. An apparatus for insertion and extraction of an implant in a desired anatomical location comprising:

an elongate outer housing having a distal end and a proximal end and defining a hollow portion in at least the distal end thereof, a portion of the distal end being comprised of a plurality of expandable gripping segments;

an expansion member housed in the hollow portion of the outer housing;

an actuation assembly for moving the expansion member between an extended position wherein the expansion member expands the gripping segments and a retracted position wherein the gripping segments contract, the actuation assembly comprising a rotatable shell on the outer housing operatively connected to the expansion member such that rotational movement of the shell causes the expansion member to move between the extended and the retracted positions and an actuation member for converting the rotational movement of the shell into movement of the expansion; and a biasing member for biasing the expansion member in the extended position.

2. The apparatus recited in claim 1 further comprising an assembly for aligning the implant in the desired anatomical location for insertion.

3. The apparatus recited in claim 2 wherein the assembly for aligning the implant comprises:

a member for mounting to the outer housing in a desired orientation;

a first arm extending outwardly from the mounting member;

a second arm releasably connectable in a desired orientation to the first arm such that the second arm extends angularly from the first arm when connected thereto for alignment of the second arm with a remote anatomical location to thereby fix the orientation of the gripping segments relative to the desired anatomical location for insertion of the implant.

4. The apparatus recited in claim 3 wherein the second arm extends from the first arm when connected thereto at about a ninety degree angle and is connectable to the first arm in a left or a right orientation.

5. The apparatus recited in claim 3 wherein the outer housing has a mount, and the mounting member of the assembly for aligning the implant is comprised of:

a post having a slot therein for receiving the mount of the outer housing in a first or second desired orientation; and, a member for holding the mount of the housing member in the slot.

6. An apparatus for insertion and extraction of an implant in a desired anatomical location comprising:

an elongate outer housing having a distal end and a proximal end and defining a hollow portion in at least the distal end thereof, a portion of the distal end being comprised of a plurality of expandable gripping segments;

an expansion member housed in the hollow portion of the outer housing;

an actuation assembly for moving the expansion member between an extended position wherein the expansion member expands the gripping segments and a retracted position wherein the gripping segments contract, the actuation assembly comprising a rotatable shell on the outer housing operatively connected to the expansion member such that rotational movement of the shell causes the expansion member to move between the extended and the retracted positions and an actuation member for converting the rotational movement of the shell into movement of the expansion member, the actuation member comprising a rotatable sleeve affixed to the shell for movement therewith, the sleeve having opposing semi-spiral pathways in the surface thereof and a pin operatively attached to a proximal end of the expansion member, the pin having opposing ends for sliding engagement with the pathways.

7. The apparatus recited in claim 1 further comprising a cap on the proximal end of the outer housing to provide an impact surface.

8. The apparatus recited in claim 1 wherein the expansion member is an elongate rod having a distal end and a proximal end, the distal end having a beveled edge and the proximal portion having a member operatively connected to the actuation member and being configured for cooperation with the hollow portion of the outer housing for limiting the movement of the expansion member in the extended direction.

9. An apparatus for insertion and extraction of an implant in a desired anatomical location comprising:

an elongate outer housing having a distal end and a proximal end and defining a hollow portion in at least the distal end thereof, a portion of the distal end being comprised of a plurality of expandable gripping segments;

an elongate rod housed in the hollow portion of the outer housing, the elongate rod having a distal end and a proximal end, the distal end having a beveled edge and the proximal portion having a member operatively connected to the actuation member and being configured for cooperation with the hollow portion of the outer housing for limiting the movement of the elongate rod in the extended direction;

an actuation assembly for moving the elongate rod between an extended position wherein the elongate rod expands the gripping segments and a retracted position wherein the gripping segments contract, the actuation assembly comprising a rotatable shell on the outer housing operatively connected to the elongate rod such that rotational movement of the shell causes the elongate rod to move between the extended and the retracted positions and an actuation member for converting the rotational movement of the shell into movement of the elongate rod, the elongate rod comprising a rotatable sleeve affixed to the shell for movement therewith, the sleeve having opposing semi-spiral pathways in the surface thereof and a pin operatively attached to the proximal end of the elongate rod, the pin having opposing ends for sliding engagement with the pathways such that rotation of the shell and the sleeve slides the pin distally or proximally in the pathways for movement of the elongate rod in the extended or retracted positions, respectively.

10. The apparatus recited in claim 8 wherein the gripping segments each have an inner ramped surface for sliding contact with the beveled edge of the distal end of the expansion member and a flared annular outer perimeter for locking engagement with the implant.

11. The apparatus recited in claim 10 wherein the implant is an acetabular cup having an outer surface, a generally concave inner surface, and an annular groove formed in the inner surface configured for locking engagement with the flared annular outer perimeter of the gripping segments when the gripping segments are inserted in the groove and the expansion member is in the extended position.

12. The apparatus recited in claim 9 wherein the elongate rod is moved between the extended position and the retracted position by rotating the shell through the arc of an angle of about ninety degrees.

13. An implant assembly comprising:

an acetabular cup implant having an outer surface, a generally concave inner surface, and an annular groove formed in the inner surface;

a tool for inserting and removing the implant from a desired anatomical location comprising:

(a) an elongate outer housing having a distal end and a proximal end and defining a hollow portion in at least the distal end thereof, the distal end being comprised of a plurality of expandable gripping segments for engagement with the groove of the implant;

(b) an expansion member housed in the hollow portion of the outer housing;

(c) an actuation assembly for moving the expansion member between an extended position wherein the expansion member expands the gripping segments for locking engagement with the groove of the implant and a retracted position wherein the gripping segments contract for release of the gripping segments from the groove of the implant, the actuation assembly comprising a rotatable shell on the outer housing operatively connected to the expansion member such that rotational movement of the shell causes the expansion member to move between the extended and the retracted positions and an actuation member for converting the rotational movement of the shell into movement of the expansion member;

(d) an assembly for aligning the implant in the desired anatomical location for insertion; and (e) a biasing member for biasing the expansion member in the extended position.

14. The apparatus recited in claim 1 wherein the biasing member is a spring.

15. The assembly recited in claim 13 wherein the expansion member is an elongate rod having a distal end and a proximal end, the distal end having a beveled edge and the proximal portion having a member operatively connected to the actuation member and being configured for cooperation with the hollow portion of the outer housing for limiting the movement of the expansion member in the extended direction.

16. An implant assembly comprising:

an acetabular cup implant having an outer surface, a generally concave inner surface, and an annular groove formed in the inner surface;

a tool for inserting and removing the implant from a desired anatomical location comprising:

(a) an elongate outer housing having a distal end and a proximal end and defining a hollow portion in at least the distal end thereof, the distal end being comprised of a plurality of expandable gripping segments for engagement with the groove of the implant;

(b) an elongate rod housed in the hollow portion of the outer housing, the elongate rod having a distal end and a proximal end, the distal end having a beveled edge and the proximal portion having a member operatively connected to the actuation member and being configured for cooperation with the hollow portion of the outer housing for limiting the movement of the elongate rod in the extended direction;

(c) an actuation assembly for moving the elongate rod between an extended position wherein the elongate rod expands the gripping segments for locking engagement with the groove of the implant and a retracted position wherein the gripping segments contract for release of the gripping segments from the groove of the implant, the actuation assembly comprising a rotatable shell on the outer housing operatively connected to the elongate rod such that rotational movement of the shell causes the elongate rod to move between the extended and the retracted positions and an actuation member for converting the rotational movement of the shell into movement of the elongate rod, the actuation member comprising a rotatable sleeve affixed to the shell for movement therewith, the sleeve having opposing semi-spiral pathways in the surface thereof and a pin operatively attached to the proximal end of the elongate rod, the pin having opposing ends for sliding engagement with the pathways such that rotation of the shell and the sleeve slides the pin distally or proximally in the pathways for movement of the elongate rod in the extended or retracted positions, respectively; and (d) an assembly for aligning the implant in the desired anatomical location for insertion.

17. The assembly recited in claim 15 wherein the gripping segments each have an inner ramped surface for sliding contact with the beveled edge of the distal end of the expansion member and a flared annular outer perimeter for locking engagement with the annular groove of the implant.

18. The assembly recited in claim 17 wherein the annular groove has curved surfaces complementary to the flared annular outer perimeter of the gripping segments for locking engagement with the gripping segments when the gripping segments are inserted in the groove and the expansion member is in the extended position.

19. The assembly recited in claim 13 wherein the expansion member is moved between the extended position and the retracted position by rotating the shell through the arc of an angle of about ninety degrees.

20. The assembly recited in claim 13 wherein the assembly for aligning the implant comprises:

a member for mounting to the outer housing in a desired orientation;

a first arm extending outwardly from the mounting member; and, a second arm releasably connectable in a desired orientation to the first arm such that the second arm extends angularly from the first arm when connected thereto for alignment of the second arm with a remote anatomical location to thereby fix the orientation of the gripping segments relative to the desired anatomical location for insertion of the implant.

* * * * *